(12) United States Patent
Goto et al.

(10) Patent No.: US 8,215,175 B2
(45) Date of Patent: Jul. 10, 2012

(54) QUANTITATIVE EVALUATION DEVICE OF ATOMIC VACANCIES EXISTING IN SILICON WAFER, METHOD FOR THE DEVICE, SILICON WAFER MANUFACTURING METHOD, AND THIN-FILM OSCILLATOR

(75) Inventors: Terutaka Goto, Niigata (JP); Hiroshi Kaneta, Niigata (JP); Yuichi Nemoto, Niigata (JP)

(73) Assignee: Niigata University, Niigata (JP)

( * ) Notice: Subject to any disclaimer, the term of this patent is extended or adjusted under 35 U.S.C. 154(b) by 323 days.

(21) Appl. No.: 12/666,869
(22) PCT Filed: Jul. 2, 2008
(86) PCT No.: PCT/JP2008/061987
§ 371 (c)(1), (2), (4) Date: Mar. 3, 2010
(87) PCT Pub. No.: WO2009/005087
PCT Pub. Date: Jan. 8, 2009

(65) Prior Publication Data
US 2010/0186512 A1    Jul. 29, 2010

(30) Foreign Application Priority Data

Jul. 3, 2007 (JP) .................................. 2007-175679
Mar. 31, 2008 (JP) .................................. 2008-093276

(51) Int. Cl.
*G01N 29/07* (2006.01)
(52) U.S. Cl. .................. 73/632; 73/597; 73/606
(58) Field of Classification Search .......... 73/632, 73/597, 606; 438/14
See application file for complete search history.

(56) References Cited

U.S. PATENT DOCUMENTS

| 6,221,743 B1* | 4/2001 | Fujikawa et al. | 438/530 |
| 6,849,901 B2* | 2/2005 | Falster | 257/347 |
| 6,930,375 B2* | 8/2005 | Falster et al. | 257/618 |
| 7,048,824 B1* | 5/2006 | Werfel et al. | 156/345.11 |
| 8,037,761 B2* | 10/2011 | Goto et al. | 73/597 |
| 2010/0111802 A1* | 5/2010 | Umeno et al. | 423/325 |

FOREIGN PATENT DOCUMENTS

| JP | 07174742 A | 7/1995 |
| WO | 03078889 A1 | 9/2003 |

OTHER PUBLICATIONS

Goto, et al, 2006. "Observation of Low-Temperature Elastic Softening due to Vacancy in Crystalline Silicon". Journal of the Physical Society of Japan 75(4): 044602-1-044602-6. Yamada-Kaneta, et al, 2006. "Vacancies in defect-free zone of point-defect-controlled CZ silicon observed by low-temperature ultrsonic measurements". Materials Science and Engineering B 134: 240-243.
Goto, et al, 2006. "Direct observation of vacancy in silicon using sub-Kelvin ultrasonic measurements". Materials Science and Engineering B 134: 233-239.
Goto, et al, 2006. "Observation of Vacancy in High Purity Silicon Crystal Using Low-Temperature Ultrasonic Measurements". ECS Transactions 3(4): 375-385.

* cited by examiner

Primary Examiner — J M Saint Surin
(74) Attorney, Agent, or Firm — McDermott Will & Emery LLP

(57) ABSTRACT

A quantitative evaluation device and method of an atomic vacancy, which are capable of efficiently and quantitatively evaluating an atomic vacancy existing in a silicon wafer. A quantitative evaluation device 1 is equipped with a detector 5 including an ultrasonic generator 27 and an ultrasonic receiver 28, a silicon sample 6 formed with the ultrasonic generator 27 and the ultrasonic receiver 28 on a silicon wafer 26 comprising perfect crystal silicon, a magnetic force generator 4 for applying an external magnetic field to the silicon sample 6, and a cooler 3 capable of cooling and controlling the silicon sample 6 to a range of temperatures lower than or equal to 50K. The ultrasonic generator 27 and the ultrasonic receiver 28 are each equipped with a transducer 30 including a thin film oscillator 31 formed from a high-polymer material with a physical property capable of following an expanding action of a silicon wafer 26 in association with a temperature drop in the above range of the temperatures and whose molecular axes are oriented in the direction of an electric field when decreasing temperature with the electric field applied thereto and further, including electrodes 32, 33 for applying an electric field to the thin film oscillator 31.

11 Claims, 13 Drawing Sheets

FIG.7
(a)
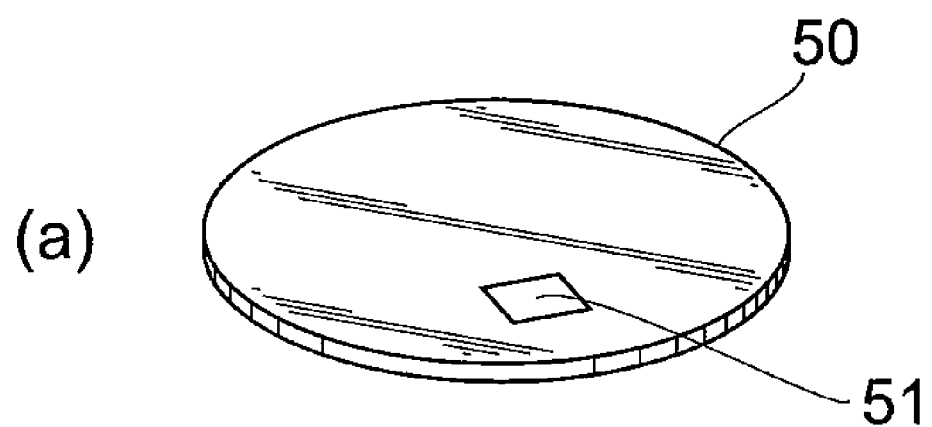
(b)
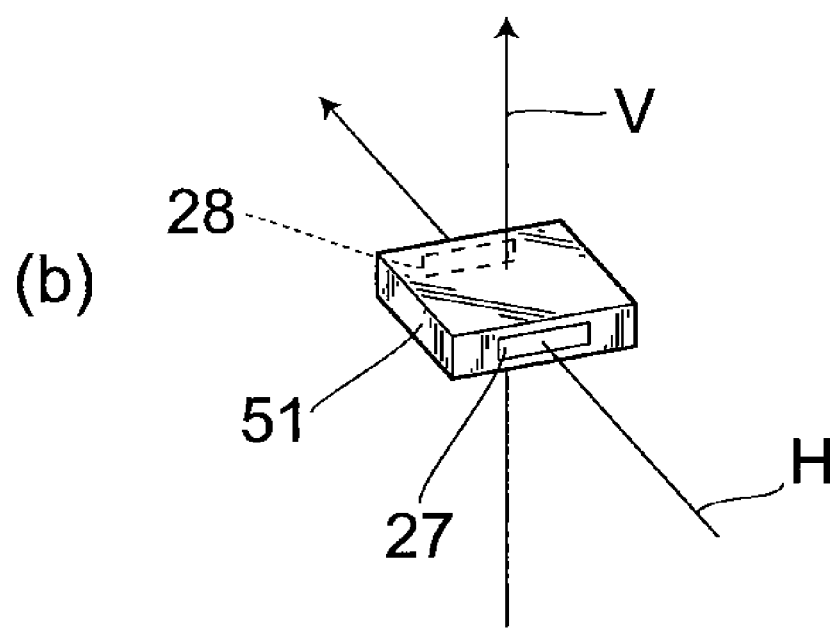

QUANTITATIVE EVALUATION DEVICE OF ATOMIC VACANCIES EXISTING IN SILICON WAFER, METHOD FOR THE DEVICE, SILICON WAFER MANUFACTURING METHOD, AND THIN-FILM OSCILLATOR

CROSS-REFERENCE TO PRIOR APPLICATION

This is the U.S. National Phase Application under 35 U.S.C. §371 of International Patent Application No. PCT/JP2008/061987 filed Jul. 2, 2008, which claims the benefit of Japanese Patent Application No. 2007-175679 filed Jul. 3, 2007, and Japanese Patent Application No. 2008-093276 filed Mar. 31, 2008, all of which are entirely incorporated by reference herein. The International Application published in Japanese on Jan. 8, 2009 as WO 2009/005087 A1 under PCT Article 21(2).

TECHNICAL FIELD

The present invention relates to a quantitative evaluation device and method of atomic vacancies existing in a silicon wafer, which are capable of direct and quantitative evaluation of a type and concentration of atomic vacancies existing in a silicon wafer manufactured by means of the Czochralski method (CZ method) or the float-zone method (FZ method) employed in the semiconductor industry.

BACKGROUND

Recently, a semiconductor element (LSI: Large Scale Integration) represented by a DRAM and a flash memory is expanding its range of functions and enhancing its quality in association with the advancing communication equipment or the like, and a demand therefore is rapidly increasing (twice in two years) by the widespread use of a mobile phone, a portable music player or the like. In response to this situation, the demand for a silicon wafer as a material for a semiconductor element is also rapidly increasing. Therefore, in order to meet this increasing demand, a technique for enabling the efficient production of high-quality silicon wafers is sought after. In fact, in the semiconductor industry, a silicon wafer is produced generally by means of the Czochralski (CZ) method or the float-zone method. In the silicon wafers formed by these methods, lattice defects are involved at a certain rate. This lattice defect is a point defect made in the combination of an interstitial atom and an atomic vacancy, which mainly exists in the order of a missing one atom in a lattice. When this point defect forms an aggregate, the nature of a silicon wafer is adversely affected. Accordingly, an anneal wafer, an epitaxial wafer and a perfectly crystallized silicon wafer are in use for a so-called high-end device that is used for communication equipment or the like as described above.

Inconveniently, in an anneal wafer, an annealing process is applied to the surface of a substrate wafer to remove defects on the outermost surface of the wafer. Besides, in an epitaxial wafer, an epitaxial layer is formed on the wafer whose impurity concentration and thickness have been precisely controlled. That means, in producing anneal and epitaxial wafers, a secondary process has to be applied to a silicon wafer cut out from a silicon ingot. Hence, the number of production steps increases, leading to the difficulty in efficiently producing a silicon wafer. Besides, in anneal and epitaxial wafers, in addition to the difficulty described above, there exists another problem that the secondary process is hard to apply to an upper surface of a large-diameter wafer.

For these reasons, in recent years, a perfectly crystallized silicon wafer in which interstitial atoms have been removed to allow only atom vacancies to remain is considered to offer promising prospects. Even with the perfectly crystallized silicon wafer, however, in order to improve its yield ratio, an atom-vacancy- and an interstitial-atom-rich region have to be determined respectively inside a crystal ingot. Further, even in a single atom-vacancy-rich region, the distribution of the concentration of the atom vacancy needs to be evaluated in advance.

Accordingly, a quantitative evaluation of the concentration of atom vacancy based on the ultrasonic measurement is required for developing a growth technique of a CZ silicon crystal ingot with controlled point defects. A concentration of atomic vacancies existing within the perfectly crystallized silicon wafer manufactured by slicing the CZ silicon crystal ingot is evaluated by the ultrasonic measurement in advance, and hence, control of properties is possible in manufacturing a device by using the perfectly crystallized silicon wafer, and thus, it is expected to make a considerable contribution to improving the yield ratio of the device.

A atomic vacancy analyzing device using the ultrasonic measurement has been proposed in the past. According to this atomic vacancy analyzing device, an external magnetic field is applied to a silicon sample and then an ultrasonic wave is allowed to pass through the silicon sample which is being cooled, thus obtaining a curve indicating a relationship between a change in ultrasonic sound velocity or its absorption and a cooling temperature. Then, based on the amount of drop in the obtained steep drop curve, the concentration of defects in atomic vacancy is determined. In the silicon sample, a oscillator comprising, e.g., $LiNbO_3$ adheres via an adhesive to the surface of a silicon wafer as a testing sample. By applying an alternating voltage to the oscillator, the generation and reception of an ultrasonic pulse are realized.

Unfortunately, a silicon wafer slightly expands at about 200K or lower, while the oscillator comprising $LiNbO_3$ contracts at low temperatures. Hence, if such a method is employed that the typically employed oscillator comprising $LiNbO_3$ is allowed to adhere to a silicon wafer, the differential thermal expansion causes the adhered portion between the surface of a silicon wafer and the oscillator to exfoliate from each other. Accordingly, it has been learnt that if a transducer utilizing the oscillator comprising $LiNbO_3$ is employed, then the change in ultrasonic sound velocity in a silicon wafer can not be stably measured.

On the other hand, instead of the oscillator comprising $LiNbO_3$, a quantitative evaluation device of an atomic vacancy has been proposed, which utilizes a thin film oscillator comprising zinc oxide (ZnO). In order to generate and receive an ultrasonic pulse, the silicon wafer, being a material under test, is provided with an ultrasonic generator on its one side and an ultrasonic receiver on its other side. These ultrasonic generator and ultrasonic receiver each comprise a transducer composed of the above oscillator comprising the ZnO thin film and electrodes provided on both sides of the silicon wafer, with the thin film oscillator being sandwiched between the electrodes. One electrode is provided on the silicon wafer via a chrome thin film. Here, the ZnO thin film is formed directly by a sputtering method on the electrode so that its C axis is approximately aligned in a certain direction. Here, the C axis means a rotational symmetrical axis of a crystalline structure of the ZnO thin film.

When an alternating voltage is applied to the electrode of the ultrasonic generator provided on one surface of the silicon wafer, the thin film oscillator expands, contracts and vibrates (actually a pulse wave) to send an elastic wave (in fact, a pulse wave) into the silicon wafer. This elastic wave is detected by the ultrasonic receiver provided on the opposing surface of the silicon wafer that is to be converted into an electric signal.

As described above, by employing the ZnO thin film as an oscillator, there occurs no exfoliation in oscillator, thus exerting a profound effect capable of stably measuring an atomic vacancy existing in the silicon wafer.

SUMMARY OF THE INVENTION

In general, if the ZnO thin film oscillator is made by, for example, a sputtering method, it takes a long time to deposit the ZnO thin film. In other words, this ZnO thin film is typically formed to a 1 to 20 µm thickness, and hence, for the primary purpose of increasing the measurement precision, this thickness has to be varied in association with thickness of a measurement sample. Generally, the thinner the measurement sample, the higher frequency acoustic wave is required and hence, the ZnO thin film to must be made thinner.

A ZnO thin film of 3 to 10 µm in thickness is most frequently employed as a thin film oscillator. It takes about 12 hours to form the ZnO thin film of 10 µm in thickness by a sputtering method. It takes about 2 days to form the ZnO thin film on both sides (an obverse side and a reverse side), of a silicon wafer to form the ultrasonic generator and the ultrasonic receiver. According to the conventional arts, therefore, it takes a long period of time to form a transducer and hence it becomes difficult to mass-produce wafers within a short period of time and then evaluate the large quantity, in order to meet the increasing demand. This difficulty roots in essential shortcoming of the conventional arts that a prolonged time is required for forming a good-quality ZnO thin film, and hence, it poses an unavoidable problem as long as the ZnO thin film is employed.

As for a sputtering method, a sputtering device is generally expensive and requires a high vacuum, leading to the necessity for a complicated manufacturing process.

Accordingly, for the above reasons, when using the conventional method for forming a thin film oscillator by using the sputtering method, the quantitative evaluation of an atomic vacancy existing in the silicon wafer was difficult to perform efficiently.

With the view of the above problems, it is an object of the present invention to provide a quantitative evaluation device of an atomic vacancy capable of efficiently and quantitatively evaluating an atomic vacancy existing in a silicon wafer and further to provide a quantitative evaluation method for the same.

The invention according to a first aspect of the present invention is characterized by a quantitative evaluation device comprising a silicon sample formed with an ultrasonic generator and an ultrasonic receiver on a silicon wafer, a magnetic force generator for applying an external magnetic field to the silicon sample, a cooler capable of cooling the silicon sample to a range of temperatures lower than or equal to 50K, and a detector for detecting a phase difference between an ultrasonic pulse generated from the ultrasonic generator and a measured wave pulse created by allowing the ultrasonic pulse to propagate within a silicon wafer to be received in the ultrasonic receiver, wherein the ultrasonic generator and the ultrasonic receiver are each equipped with a transducer including a thin film oscillator and electrodes for applying an electric field to the thin film oscillator, the thin film oscillator having a physical property capable of following an expanding action of a silicon wafer in association with a temperature drop in the range of the temperatures and besides made up of a high-polymer material having the nature of generating orientations of molecular axes in any one of the following cases where: it is solidified; solidified and then heated; and solidified, heated and then cooled.

A second aspect of the present invention is characterized in that the thin film oscillator is made up of a high-polymer material having the nature of being solidified with the molecular axes oriented in the direction of an electric field applied to the high-polymer material, and that at the same time, said orientations of molecular axes is maintained even after the electric field has been removed.

A third aspect of the present invention is characterized in that in a highly-heated state at temperatures equal to or higher than 50 degrees C. and lower than or equal to 500 degrees C., an electric field is applied to the thin film oscillator to orient molecular axes of the thin film oscillator in the direction of the electric field.

A fourth aspect of the present invention is characterized in that the high-polymer material is PVDF or P (VDF/TrFE).

A fifth aspect of the present invention is characterized in that the thin film oscillator is 0.1 to 30 µm in thickness.

A sixth aspect of the present invention is characterized in that the ultrasonic pulse is allowed to propagate in the direction of a crystal orientation, in which a ratio of an elastic constant $C_{44}$, is large enough, and then, the measured wave pulse is received in the ultrasonic receiver to detect a phase difference between the ultrasonic pulse and the measured wave pulse.

A seventh aspect of the present invention is characterized in that any one of a gold thin film, a titanium thin film, an aluminum thin film and a copper thin film is formed between a surface of the thin film oscillator and a surface of the silicon sample.

An eight aspect of the present invention is characterized in that the ultrasonic generator and the ultrasonic receiver employ an ultrasonic pulse width of 10 µs or less.

A ninth aspect of the present invention is characterized by a quantitative evaluation method comprising: an orientation treatment step of generating orientations of molecular axes in any one of cases where a thin film oscillator is solidified; it is heated after being solidified; and it is cooled after being solidified and heated, with respect to a silicon sample formed with an ultrasonic generator and an ultrasonic receiver each including the thin film oscillator made up of a high-polymer material having a physical property capable of following an expanding action of a silicon wafer in association with a temperature drop in a range of temperatures lower than or equal to 50K; and a detection step of detecting a phase difference between an ultrasonic pulse and a measured wave pulse, said detection being performed such that in a range of temperatures lower than or equal to 50K, an external electric field is applied to an ultrasonic generator to generate an ultrasonic pulse in the ultrasonic generator and then said ultrasonic pulse is allowed to propagate within a silicon wafer to create a measured wave pulse, which is received in the ultrasonic receiver, thus, detecting a phase difference between said ultrasonic pulse and measured wave pulse.

A tenth aspect of the present invention is characterized in that the quantitative evaluation method includes an evaluation process for quantitatively evaluating an atomic vacancy existing in a silicon wafer by using the quantitative evaluation method according to the ninth aspect.

An eleventh aspect of the present invention is characterized in that a thin film oscillator has the physical property capable of following the expanding action of a silicon wafer in association with a temperature drop in the range of temperatures lower than or equal to 50K, and is made up of high-polymer material having the nature of generating orientations of molecular axes in any one of the cases where the thin film oscillator is solidified, where after being solidified, the thin film oscillator is heated, and where after being solidified, the thin film oscillator is heated and then is cooled.

A twelfth aspect of the present invention is characterized in that the thin film oscillator is used for the ultrasonic generator and the ultrasonic receiver that are utilized for a quantitative evaluation device of an atomic vacancy existing in a silicon wafer and are each equipped with a detector including the ultrasonic generator and the ultrasonic receiver, a silicon sample formed with the ultrasonic generator and the ultrasonic receiver in a silicon wafer, a magnetic force generator for applying an external magnetic field to the silicon sample, and a cooler capable of cooling the silicon sample to a range of temperatures lower than or equal to 50K, and further the thin film oscillator is made up of a high-polymer material having the nature of being solidified with its molecular axes oriented in the direction of an electric field applied to the high-polymer material and then holding the orientations of the molecular axes even after removing the electric field.

According to the quantitative evaluation device of the first aspect, the thin film oscillator is made up of a high-polymer material and therefore, can be provided on the silicon wafer. As a result, when compared to the conventional thin film oscillator formed with the ZnO thin film made by a physical vapor-deposition technique such as a sputtering method, a uniform thin film can be formed in a short period of time with dramatic ease. Hence, an atomic vacancy existing in a silicon wafer can be efficiently evaluated. Furthermore, in the conventional thin film oscillator formed with the ZnO thin film, the film could be formed into 0.5 to 10 μm in thickness. In the present invention, however, the thin film oscillator is formed from a high-polymer material and the film can be formed into as wide a range as 0.1 to 30 μm in thickness.

According to the quantitative evaluation device of the second aspect, molecular axes can be certainly oriented in a predetermined direction.

According to the quantitative evaluation device of the third aspect, a molecular axis can be more certainly oriented in a predetermined direction.

According to the quantitative evaluation device of the fourth aspect, the ultrasonic pulse can be more certainly generated.

According to the quantitative evaluation device of the fifth aspect, a measurable ultrasonic sound wave can be generated.

According to the quantitative evaluation device of the sixth aspect, the ultrasonic pulse is allowed to propagate in the direction of a crystal orientation where a $C_{44}$ ratio is large and the measured wave pulse is received in the ultrasonic receiver and thereby, an atomic vacancy concentration within a wafer can be more certainly evaluated by detecting the phase difference between the ultrasonic pulse and the measured wave pulse thus, permitting an atomic vacancy in the wafer to be quantitatively evaluated with more precision.

According to the quantitative evaluation device of the seventh aspect, the exfoliation can be prevented in cooling and besides, electric conductivity can be enhanced.

According to the quantitative evaluation device of the eighth aspect, adjacent pulses are mutually discriminated with a certainty.

According to the quantitative evaluation device of the ninth aspect, the thin film oscillator is made up of a high-polymer material and thereby, the thin film oscillator can be formed with a dramatic ease and within a short period of time as compared to the conventional oscillator formed with the ZnO thin film by a physical vapor-deposition method and hence, an atomic vacancy existing in a silicon wafer can be efficiently and quantitatively evaluated.

According to the silicon wafer manufacturing method of the tenth aspect, a high-quality silicon wafer can be efficiently manufactured within a short period of time.

According to the thin film oscillator of the eleventh aspect, as compared to the conventional oscillator formed with the ZnO thin film made by using a physical vapor-deposition method, the thin film oscillator is made up of a high-polymer material and thereby, a uniform thin-film can be formed with dramatic ease and within a short period of time and hence, an atomic vacancy existing in a silicon wafer can be effectively and quantitatively evaluated.

According to the thin film oscillator of the twelfth aspect, an ultrasonic pulse can be more certainly generated.

BRIEF DESCRIPTION OF THE DRAWINGS

FIG. 7 illustrates a relationship between the crystal orientation and measuring direction of a silicon wafer in the quantitative evaluation method according to the present invention.

DETAILED DESCRIPTION

Figure 1:
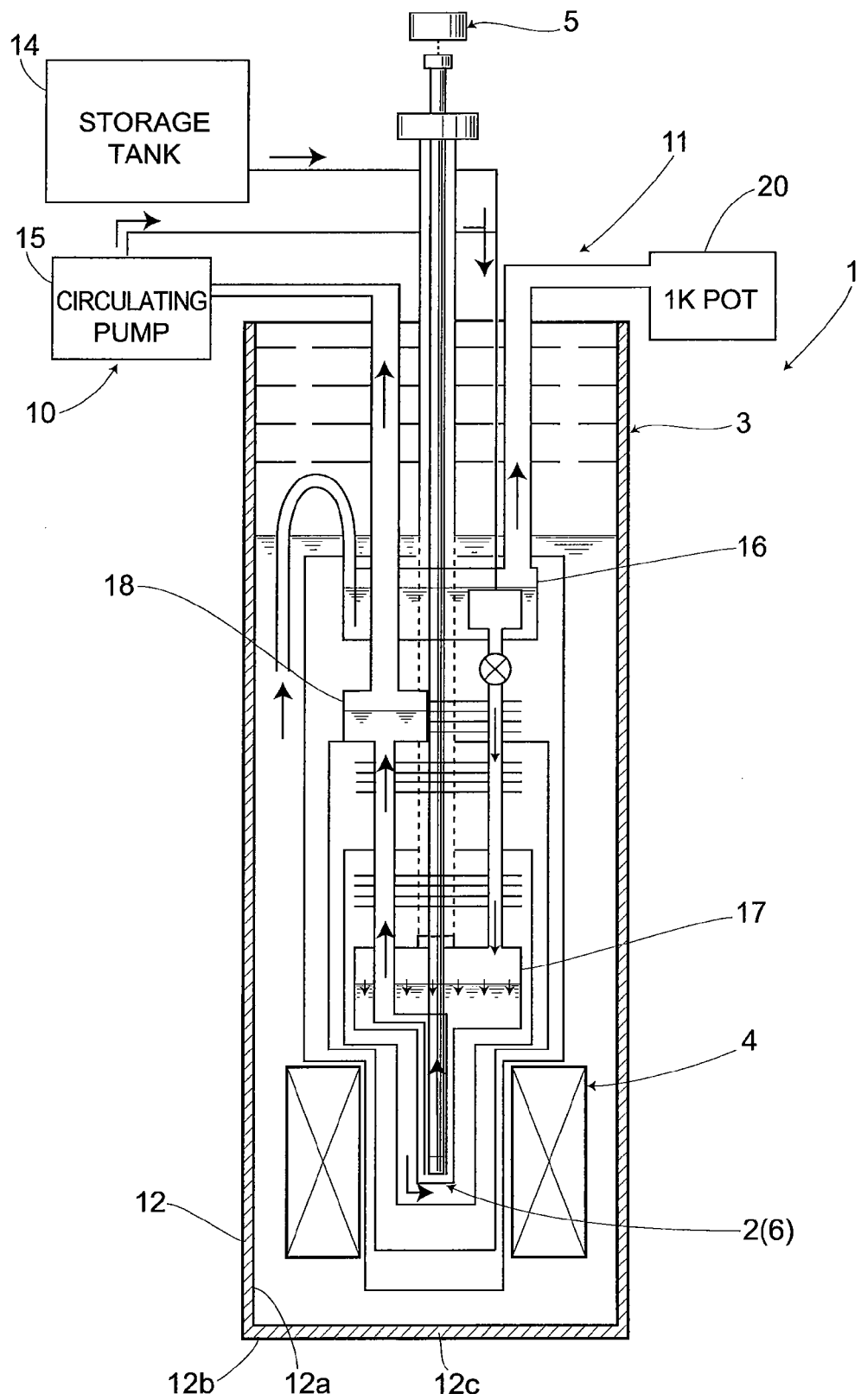
FIG. 1 is a schematic view illustrating a quantitative evaluation device of an atomic vacancy existing in a silicon wafer, according to the present embodiment.

A quantitative evaluation device 1 for an atomic vacancy existing in a silicon wafer, according to the present invention is described with reference to the accompanied drawings.

The quantitative evaluation device 1 is equipped with a sample holder 2, a dilution refrigerator 3 for cooling means, a magnetic force generator 4, and a detector 5. As a whole, the quantitative evaluation device 1 cools a silicon sample 6 disposed on the sample holder 2 with an external magnetic field applied to the silicon sample 6 and then can detect an acoustic velocity of an ultrasonic pulse propagated within a silicon wafer described below.

The magnetic force generator 4 is arranged, in a surrounding position where the silicon sample 6 has been set, to apply the external magnetic field to the silicon sample 6 as the magnetic force generator 4, e.g., a superconducting electromagnet is available. In the magnetic force generator 4, in order to detect an acoustic velocity of the ultrasonic pulse propagated within the silicon wafer, it is desirable that magnetic force is controllable within the compass of 0 to 20 tesla with the external magnetic field applied to the silicon wafer 6, as needed. A type of an atomic vacancy isolated within a silicon wafer, e.g., can be specified by applying an external magnetic force thereto, as described below.

The dilution refrigerator 3 can cool and control the silicon sample 6 disposed in the sample holder 2 to a range of temperatures lower than or equal to 50K. In the present embodiment, the dilution refrigerator 3 comprises two systems of a $^3$He system 10 and a $^4$He system 11 to enable an inside of a dewar 12 to be cooled to a preset desired temperature. The dewar 12 includes a double structure comprising inner and outer layers 12a, 12b and then a vacuum space 12c is formed between the inner and outer layers 12a, 12b. Inside the dewar 12, a liquid $^4$He is stored.

The $^3$He system 10 is structured so as to obtain cooling performance as the dilution refrigerator 3. The $^3$He system 10 is equipped with a storage tank 14, a circulating pump 15, a condenser 16, a mixer 17 and a separator 18. The circulating pump 15 is different from a usual pump and is structured so that a $^3$He gas is prevented from escaping to the atmosphere. The condenser 16 cools the $^3$He gas sent out of the circulating pump 15 to obtain a $^3$He liquid.

The mixer 17 is a portion of the lowest-temperature in the dilution refrigerator 3. An interface of a compound liquid of the phase-separated $^3$He and $^4$He exists inside the mixer 17. An upper half inside the mixer 17 is a $^3$He-dense region that is constantly supplied from the condenser 16. A lower half inside the mixer 17 is a $^3$He-thin region (its concentration is about 6% and the residual is superfluid $^4$He) to communicate with the separator 18. In this mixer 17, $^3$He is forcibly allowed to move from the $^3$He-dense region with large entropy to the $^3$He-thin region with little entropy. An entropy difference generated at this time causes the dilution refrigerator 3 to generate cooling effect.

The separator 18 can selectively evaporate $^3$He in the $^3$He-thin region. The separator 18 is held at a given temperature (e.g., lower than or equal to 0.8K). As a result, the separator 18 evaporates only $^3$He by using a phenomenon where the steam pressure of $^3$He is kept at a finite value that is contrary to a phenomenon where the steam pressure of $^4$He is 0.

The $^4$He system 11 can liquidize the $^3$He gas. The $^4$He system 11 is equipped with a 1 k pot 20 including an air displacement pump. The $^4$He system 11 obtains cooling capability by exhausting air with the air displacement pump inside the 1K pot 20. In the present embodiment, by directly taking in the $^4$He liquid of 4.2K from the dewar 12 via the condenser 16, a continuous operation is possible, thus liquidizing the $^3$He gas in the condenser 16.

In addition, FIG. 1 shows the structure in which the sample holder 2 in which the silicon sample 6 has been set is immersed within the compound liquid of $^3$He and $^4$He inside the mixer 17 to be directly cooled. Not limiting to this structure, however, a member for forming the cooled mixer 17 is composed of a material with high thermal conductivity and its thermal conduction from the member for forming the mixer 17 is utilized to enable the silicon sample 6 to be indirectly cooled. In the structure like this, particularly cooling temperature range can be advantageously extended to a high-temperature range.

The detector 5 generates an ultrasonic pulse to the surface of a silicon wafer and propagates the generated ultrasonic pulse within a silicon wafer to create and receive a measured wave pulse, thus allowing an acoustic velocity of the ultrasonic pulse propagated within the silicon wafer to be detected.

Figure 2:
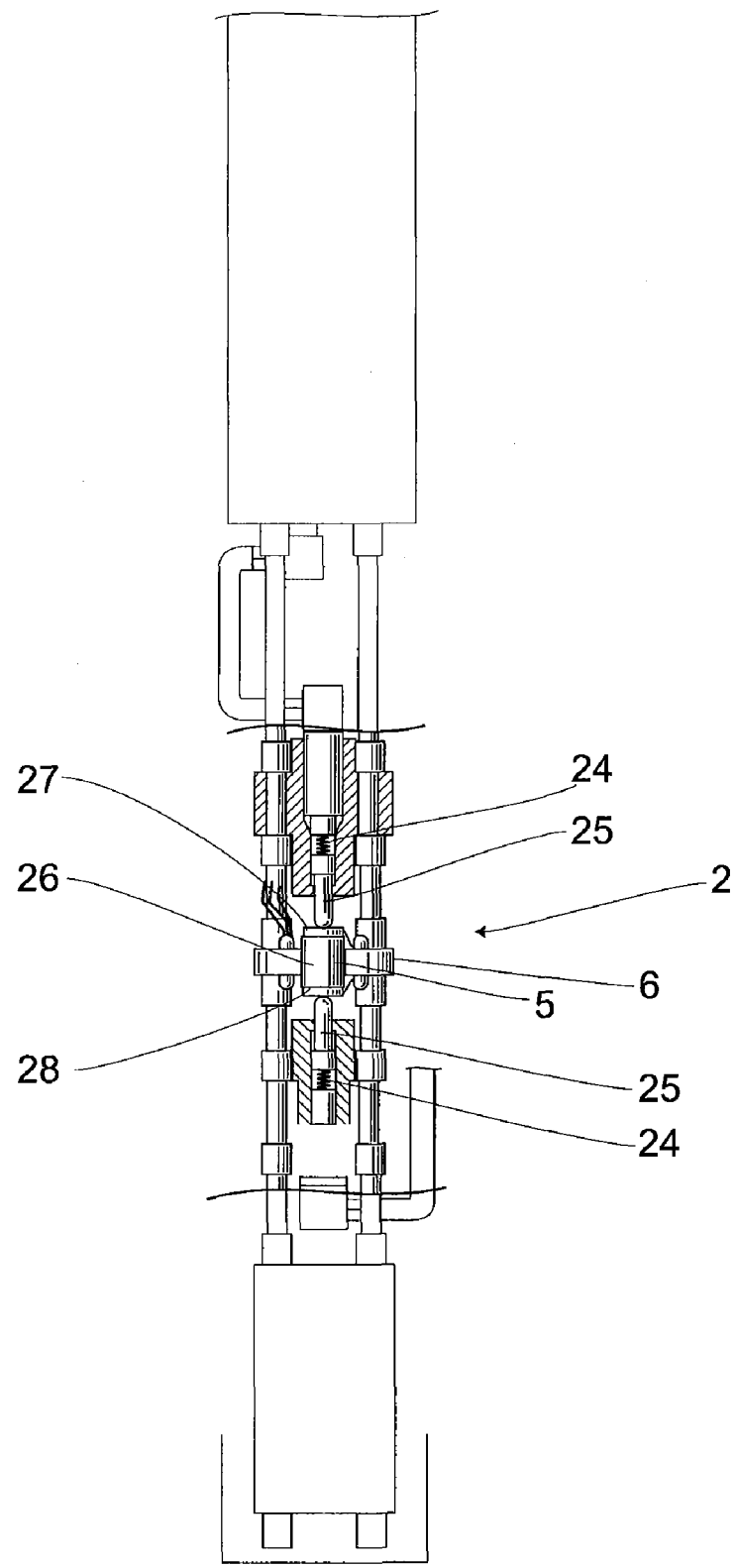
FIG. 2 is an enlarged view illustrating the part of a sample holder in which a silicon sample is set, according to the present embodiment.

As shown in FIG. 2, the sample holder 2 includes a pair of pins 25 axially energized by coil springs 24. The thus structured sample holder 2 sandwiches the silicon sample 6 between a pair of the pins 25 to hold the silicon sample 6.

In the present invention, the silicon sample 6 comprises a silicon wafer 26, an ultrasonic generator 27 provided on one surface of the silicon wafer 26 and an ultrasonic receiver 28 provided on the other surface. The ultrasonic generator 27 and the ultrasonic receiver 28 are each equipped with a transducer described later.

Figure 3:
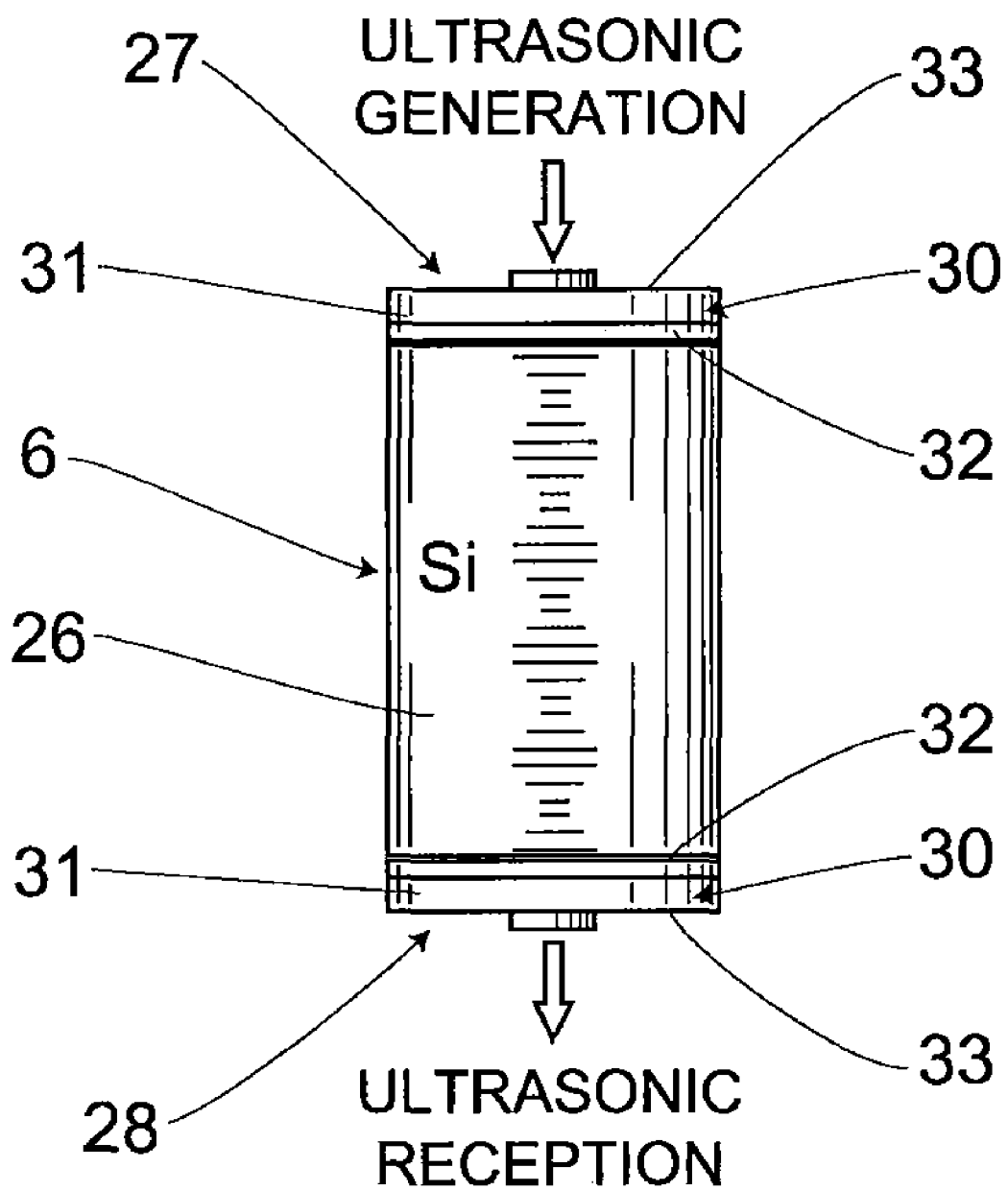
FIG. 3 is a cross-sectional view illustrating a model structure of a silicon sample according to the present embodiment.

As shown in FIG. 3, the transducer 30 comprises a thin film oscillator 31 formed into a film-like shape, an inner electrode 32 and an outer electrode 33 to apply an electric field on the thin film oscillator 31.

The thin film oscillator 31 is made up of a high-polymer material which includes large electric dipole moments in molecular chins and whose dipoles are oriented (poling) in the direction of an electric field when having applied the electric field thereto. The thin film oscillator 31 is formed by solidifying a liquid high-polymer material with a physical property capable of following an expanding action of a silicon wafer in association with a drop in temperature with the range of the above temperatures and further, has the nature of being solidified with its molecular axes oriented in the direction of an electric field applied to the high-polymer material and then holding orientations (electrolysis) of the molecular axes even after removing the electric field. Here, the molecular axis means a pair of positive and negative charges disposed at an infinitesimal distance from each other. The orientation is performed under a highly-heated state at temperatures equal to or higher than 50 degrees C. and lower than or equal to 500 degrees C. Furthermore, the physical property capable of following the expanding action of the silicon wafer 26 means that the stress generated by cubical expansion when the silicon wafer 26 is made into a low-temperature state is absorbed by the thin film oscillator 31 to thereby permit the thin film oscillator 31 to be prevented from exfoliating. In the present embodiment, the thin film oscillator 31 is made of a polymer (PVDF) of vinylidene fluoride $CH_2CF_2$ (VDF).

In addition, the present invention is not limited to the foregoing, but as any other high-polymers material like this, available are e.g., a copolymer (P(VDF/TrFE)) of VDF and trifluoroethylene CHFCF$_2$(TrFE), a copolymer (P(VDF/TeFE)) of VDF and tetrafluoroethylene CF$_2$CF$_2$(TeFE), an alternate copolymer (P(VDCN/VAc)) of vinylidene cyanide CH$_2$C(CN)$_2$ (VDCN) and acetic acid vinyl CH$_2$CHOCOCH$_3$ (VAc), a condensation polymer (NHCONH—R—NH-CONH—R')n(R,R' denote aromatic series, PU (polyurea)) of diamine and isocyanate, and fluorine resin.

In addition, PVDF is large in voltage-distortion characteristic in comparison with the other above high-polymer materials and besides, its linear range is wide in voltage-distortion characteristic. Accordingly, by being made up of PVDF, the thin film oscillator 31 allows the silicon wafer to be efficiently and quantitatively evaluated by low voltage.

It is desirable that the thin film oscillator 31 is made into 0.1 to 10 μm in thickness since a measurable ultrasonic sound wave can be generated.

A manufacturing method for the silicon sample 6 is described which is structured as described above. First, Ag or Au is deposited on one surface of a pair of opposed surfaces on the silicon wafer 26 to form the inner electrode 32. Then, the thin film oscillator 31 made up of a high-polymer material is formed on the electrode by a spin coat method. That is to say, the thin film oscillator 31 is formed in such a way that the high-polymer material dissolved in a solution is dropped on a surface of the inner electrode formed on the silicon wafer 26 and then the silicon wafer 26 is otated for the solution to be uniformly applied on the surface of the inner electrode by centrifugal force in the rotating motion. Next, Ag or Au is deposited on the thus formed thin film oscillator 31, forming the outer electrode 33.

As described above, in the present invention, the thin film oscillator 31 is made up of a high-polymer material and thereby, the thin film oscillator 31 can be formed by a spin coat method. As a result, when compared to the conventional method where the ZnO thin film was formed by a physical vapor deposition method such as a sputtering method, a uniform thin film can be formed with marked ease and over a short period of time and hence a high-quality silicon wafer 26 can be mass-produced in a short term, permitting a large quantity of the silicon wafer to be evaluated.

Incidentally, in the conventional quantitative evaluation device whose thin film oscillator comprising the ZnO thin film formed by a sputtering method, a sputtering device was generally expensive and a high vacuum state was required to cause an elaborate manufacturing process to be needed, resulting in hampering an efficient and quantitative evaluation.

In contrast to this, in the present invention, the thin film oscillator 31 is made up of a high-polymer material and thereby, the thin film oscillator 31 can be formed by a spin coat method. In the spin coat method, not only its device is inexpensive but a specific vacuum is not required to permit a manufacturing process for simplification. Accordingly, as compared to the conventional device manufactured by a sputtering method, the quantitative evaluation device according to the present invention can be formed with marked ease, enabling the quantitative evaluation to be efficiently practiced.

Further, the device is inexpensive and the efficient and quantitative evaluation can be achieved. Consequently, by utilizing the device according to the present invention, the evaluation is possible even while in a wafer production line, e.g., a wafer mass-production line.

In the conventional method where the ZnO film has been formed, the film capable of being formed was 0.5 to 10 μm in thickness, while in the method according to the present invention which forms the thin film oscillator by a spin coat method, the film can be made in as wide a range as 0.1 to 30 μm in thickness.

Furthermore, the thin film oscillator 31 is structured in this way and thereby even if the silicon wafer 26 is cooled to extremely-low temperatures not more than 50K, the thin film oscillator 31 can follow the expanding action of the silicon wafer 26, thus permitting the thin film to be prevented from exfoliating owing to the above cooling process. Accordingly, the quantitative evaluation device 1 as per the present embodiment can precisely detect the acoustic velocity of the ultrasonic pulse propagated within the silicon wafer 26. As a result, the type and existing concentration of an atomic vacancy isolated within the silicon wafer 26 can be directly, stably and quantitatively evaluated without performing an accelerated process such as increasing the concentration.

Also, any one of a gold thin film, a titanium thin film, an aluminum thin film and a copper thin film is formed between the thin film oscillator 31 and the surface of the silicon wafer 26. Hence, the exfoliation in the cooling process can be prevented and the electric conductivity can be enhanced.

Figure 4:
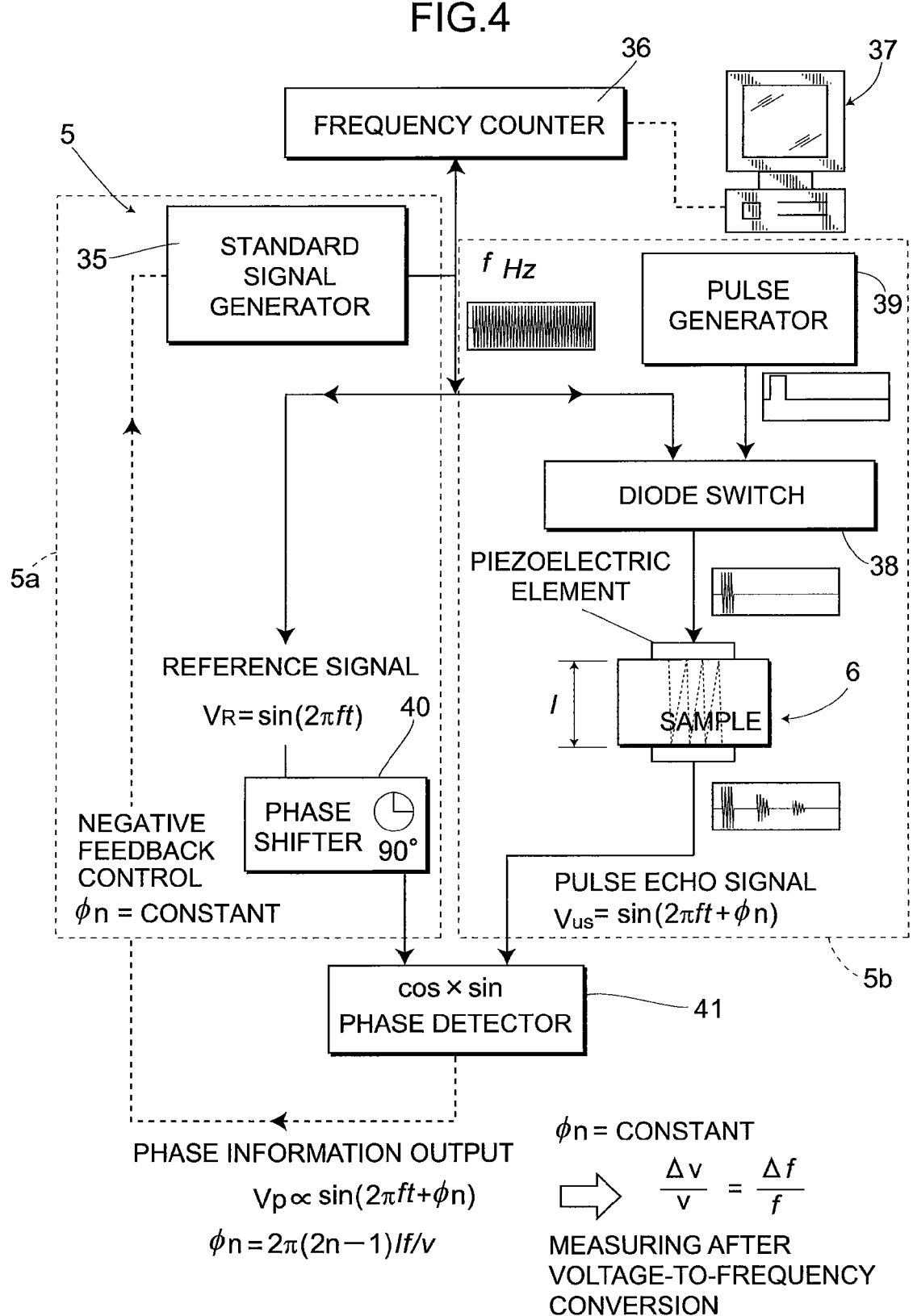
FIG. 4 is an overall structural view schematic diagram showing a method for detecting a phase difference using an ultrasonic pulse, according to the present embodiment.

The detector 5 shown in FIG. 4 can detect a phase difference between a produced reference signal by directly measuring a basic signal and a measured signal of a wave pulse measured after when the ultrasonic pulse has been allowed to propagate within the silicon wafer 26. In the present embodiment, the detector 5 is equipped with a standard signal generator 35, a frequency counter 36, a personal computer 37, a diode switch 38, a pulse generator 39, a phase shifter 40, and a phase detector 41.

The standard signal generator 35 generates the basic signal. This basic signal is branched into a reference signal system 5a and a measured signal system 5b. In addition, the frequency counter 36 measures the basic signal to output the measured result to a personal computer 37.

The standard signal system 5a is connected with the phase detector 41 via the phase shifter 40. At the same time, the measured signal system 5b is arranged with a diode switch 38 connected with a pulse generator 39 and the silicon sample 6, in sequence and is connected with the phase detector 41. The diode switch 38 divides the basic signal into a signal with a given width.

The phase detector 41 compares the reference signal based on the basic signal and the measured signal output from the silicon sample 6 to detect the acoustic velocity of the ultrasonic pulse within the silicon wafer 26.

The detector 5 thus structured measures the acoustic velocity within a silicon wafer 26 with 10 mm or less in width by using an ultrasonic pulse to enable adjacent pulses to be certainly discriminated. The detector 5 more preferably includes the means for varying a generating frequency to thereby detect zero, so as to stabilize the phase difference caused by changes in temperature, magnetic field and acoustic velocity.

The quantitative evaluation device 1 according to the present invention is desirably structured so as to be capable of simultaneously measuring phase differences both in a set of silicon samples 6 and in plural detection points in one silicon sample 6 at the same time.

Hereunder is a description of a quantitative evaluation method of an atomic vacancy existing in a silicon wafer 26, according to the present invention.

In the quantitative evaluation method according to the present invention, a silicon sample 6, formed with the ultrasonic generator 27 and the ultrasonic sound 28 on the surface of a silicon wafer 26 cut out of a given portion of a silicon ingot, is cooled at a range of temperatures lower than or equal to 25K with an external magnetic field applied to the silicon sample 6 as needed.

After that, the standard signal generator 35 generates the basic signal. This basic signal is branched into the reference signal system 5a and the measured wave signal system 5b. The basic signal of the measured wave signal 5a is divided into 0.5 µs in width by a diode switch 38.

An alternating electric field is applied by the basic signal and is divided by the diode switch 38 to a portion between the outer electrode 33 and the inner electrode 32 in the transducer 30. This alternating electric field orients the molecular axes of the thin film oscillator 31 in the direction of the electric field. So, the thin film oscillator 31 polarizes to cause the emergence of piezoelectricity, so that the ultrasonic generator 27 generates an ultrasonic pulse based on the basic signal. Thus, the basic signal is converted into a mechanical signal, that is, the ultrasonic pulse by the transducer 30 of the ultrasonic generator 27.

The ultrasonic pulse propagates from one end of the silicon wafer 26 to the other end. The ultrasonic pulse propagating within the silicon wafer 26 iteratively reflects at one and the other ends of the silicon wafer 26 to be received as the measured wave pulse in the transducer 30 of the ultrasonic receiver 28 and again is converted into an electric signal to be outputted as the measured signal.

The measured wave signal and the reference signal are compared in the phase detector 41 to measure a phase difference $\phi_n$ between the ultrasonic pulse and the measured wave pulse. Then, an acoustic velocity v was calculated by using the phase difference $\phi_n$.

$$\phi_n = 2\pi(2n-1)lf/v \quad \text{Expression 1}$$

where (2n−1)1 denotes a propagation length of an nth echo and f denotes an ultrasonic frequency.

Then, an elastic constant C was calculated from the thus calculated acoustic velocity v by using the following formula 2.

$$C = \rho v^2 \quad \text{Expression 2}$$

where $\rho$ denotes density.

Thus, the acoustic velocities v are sequentially detected from the phase differences $\phi_n$ of the ultrasonic pulses. Then, the elastic constant C in association with a decrease in cooling temperature is calculated from the acoustic velocity v to permit a type and concentration of an atomic vacancy existing in the silicon wafer 26 to be quantitatively evaluated from a decreased amount of the elastic constant C. This is due to the proportional relation between the decreased amount of the elastic constant and the concentration of atomic vacancy.

A silicon wafer <100> with 300 mm$\phi$ in diameter is d=0.775 mm in thickness. A longitudinal ultrasonic sound wave propagating in the <100> direction is v=8.4 km/sec in acoustic velocity and hence, a time taken for the ultrasonic pulse to shuttle within the silicon wafer is $t=2d/v=0.185 \times 10^{-6}$ sec. In the acoustic velocity measurement using the ultrasonic pulse, it should be taken into account so that the ultrasonic echo pulses do not overlap one another. Hence, the width of the entering ultrasonic pulse is desirably required to be smaller than $0.185 \times 10^{-6}$ sec.

In order to perform an ultrasonic measurement, at least ten or more ultrasonic waves are required in ultrasonic pulses with $0.185 \times 10^{-6}$ sec in width. Accordingly, a measuring frequency must be desirably higher than f=54 MHz.

In order to hold a large signal-to-nose ratio, a repeat count of an entering ultrasonic pulse in a short period of time must desirably be 1,000 or more (the repeat count frequency must be 1 kHz or more).

In order to convert an electric signal into an ultrasonic sound wave by the ultrasonic receiver, electric amplifiers are arranged on input and output sides. The impedances of the electric amplifier on both the sides are set in 50Ω for the sake of optimizing a carrying efficiency of a coaxial cable. Therefore, a commercially-available amplifier has input and output impedances of 50Ω. Desirably, a resonant impedance of the ZnO is adjusted as 50Ω.

Figure 5:
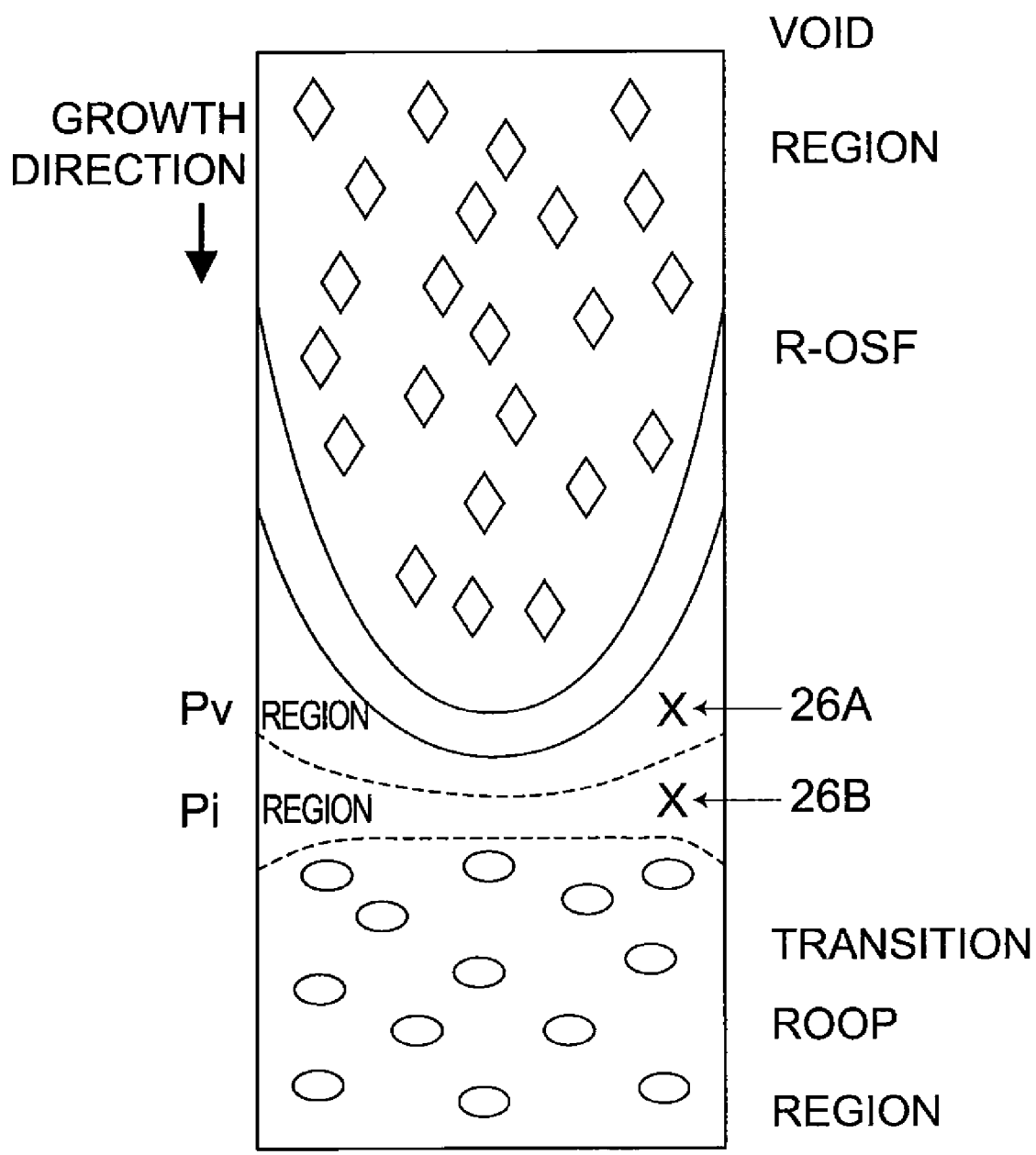
FIG. 5 is one model example of a cross-sectional view of an undoped CZ silicon ingot.

FIG. 5 shows a model cross-sectional surface of 6 inch-diameter undoped experimentally manufactured CZ silicon ingot. As is clear from FIG. 5, intrinsic point defect regions (the Pv region and the Pi region) ranging over about 3 cm were observed to exist in the center of the ingot.

Then, a silicon wafer 26 of 4 mm×4 mm×7 mm was cut out of each of the Pv and Pi regions, being the intrinsic point defect regions. The ultrasonic generator 27 and the ultrasonic receiver 28 were formed on each silicon wafer to obtain silicon samples 26A and 26B. When the silicon samples 26A, and 26B are placed in the quantitative evaluation device 1 shown in FIG. 1 and FIG. 2 and are cooled from 30K to 20 mK by the quantitative evaluation method according to the present invention and when the change in elastic constant of each of the silicon samples 26A, 26B is plotted against each of cooling temperatures, a graph shown in FIG. 6, e.g., can be obtained.

Figure 6:
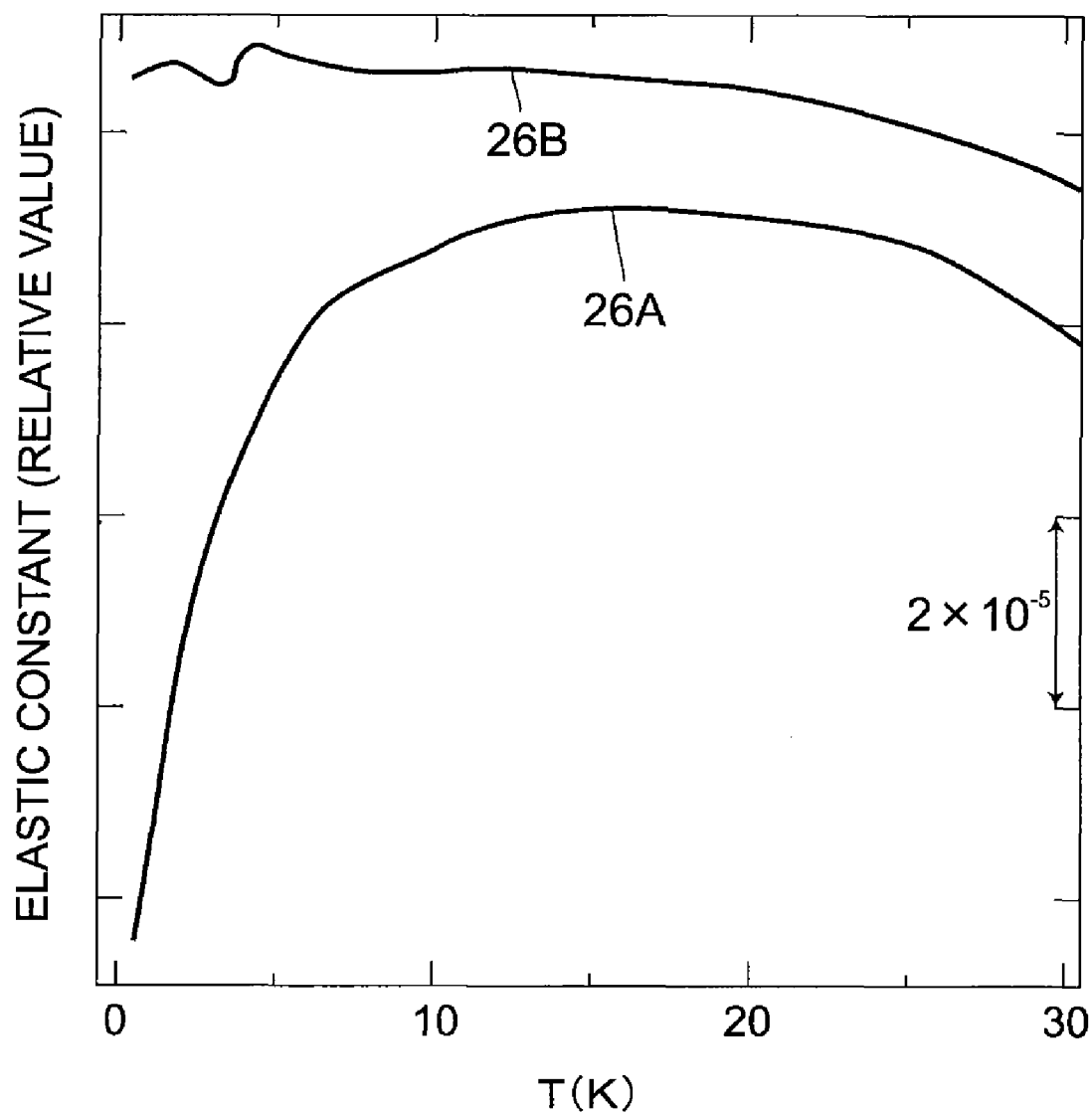
FIG. 6 is a diagram which illustrates changes in elastic constant with respect to cooling temperatures and is obtained when an atomic vacancy existing in a silicon wafer is measured by the quantitative evaluation method according to the present invention.

In the graph shown in FIG. 6, with respect to the silicon sample 26A of the Pv region which has been considered to be rich in atomic vacancy, it is demonstrated that the elastic constant remarkably decreases in proportion to a reciprocal of temperature in an ultracold temperature range of 20K to 10 mK, in other words, low-temperature softening occurs. On the other hand, with respect to the silicon sample 26B of the Pi region which has been considered to be rich in interstitial atom, it is demonstrated that there is no decrease in elastic constant.

Further, the magnetic field dependence was also investigated using a B (born)-doped FZ silicon monocrystal and a B-undoped FZ silicon monocrystal. As a result, the knowledge has been obtained that the low-temperature softening in the B-doped FZ silicon monocrystal was eliminated by applying a magnetic field, but the low-temperature softening in the B-undoped FZ silicon monocrystal was not eliminated even by applying a magnetic field. This knowledge indicates that the combination of a charged state and a distorted state which are caused by an atomic vacancy is the origin of the low-temperature softening. The atomic vacancy in the B-undoped FZ silicon monocrystal is in a unmagnetized charged state where 4 electrons have been captured, while the B-doped FZ silicon monocrystal is in a magnetized charged state where 3 electrons have been captured. A molecular orbital of an atomic vacancy is polarized into a singlet and a triplet state and the combination of an electric quadrupole and the distorted state of the triplet is considered to cause the low-temperature softening due to $C_{44}$ and $(C_{11}-C_{12})/2$. Also in the B-undoped FZ silicon monocrystal, an anti-strong-quadrupole interaction exists between atomic vacancies and a $T_d$ symmetry around an atomic vacancy is held even in the minimum temperature of 20 mK also the triplet has been degenerated and therefore, it is assumed that the fluctuation of the electric quadrupole exits.

These results show that by utilizing the knowledge that the low-temperature softening of the elastic constant, which is attributable to an atomic vacancy that has captured odd numbers (3 or 5) of electrons, has the magnetic field dependence and in contrast to this, the low-temperature softening of the elastic constant, which is attributable to an atomic vacancy that has captured even numbers (4) of electrons has no magnetic field dependence and a type of atomic vacancy can be determined from the presence or absence of the magnetic field dependence in the present invention.

In this manner, according to the quantitative evaluation device 1 and method in the present invention, the concentration of atomic vacancy can be quantitatively evaluated from the change in elastic constant in relation to the cooling temperature obtained from measurement.

The elastic constant in the direction of the crystal orientation <100> is expressed as a formula 1: where $C_B$ is expressed as a formula 2. As is clear from this formula 1, the elastic constant $C_{44}$ is not contained in the direction of the crystal orientation <100>.

$$C_L^{[100]} = C_B + \frac{4}{3}\left(\frac{C_{11} - C_{12}}{2}\right)$$ Formula 1

$$C_B = \frac{C_{11} + 2C_{12}}{3}$$ Formula 2

Likewise, the elastic constants in the directions of the crystal orientations <100> and <111> are expressed as formulae 3, 4.

$$C_L^{[110]} = C_B + \frac{1}{3}\left(\frac{C_{11} - C_{12}}{2}\right) + C_{44}$$ Formula 3

$$C_L^{[111]} = C_B + \frac{4}{3}C_{44}$$ Formula 4

As is clear from these formulae 3, 4, the term $C_{44}$ causing the low-temperature softening is included in the directions of the crystal orientations <110> and <111>. The ultrasonic pulse is allowed to propagate in the direction of the crystal orientation in which the ratio of the term $C_{44}$ is large and is received as the measured wave pulse in the ultrasonic receiver. Then, by detecting the phase difference between the ultrasonic pulse and the measured wave pulse to perform the quantitative evaluation, the concentration of atomic vacancy within a wafer can be more certainly evaluated.

Specifically, as shown in FIG. 7, a vertical direction of the silicon wafer 50 cut out of a silicon ingot corresponds to the crystal orientation <100> (refer to the arrow V in FIG. 7), while a horizontal direction of the silicon wafer 50 corresponds to the crystal orientation <110> (refer to the arrow H in FIG. 7). Accordingly, in a chip 51 obtained by further cutting the silicon wafer 50 into a given size, the ultrasonic generator 27 and the ultrasonic receiver 28 are provided on each of a pair of surfaces in the direction of the crystal orientation <110> (refer to the arrow H in FIG. 7). As a result, the ultrasonic pulse is allowed to propagate in the direction of the crystal orientation where the ratio of the term $C_{44}$ is large, thus enabling the concentration of atomic vacancy within the chip 51 to be more certainly evaluated.

The method mentioned above shows only one embodiment of the present invention and various modifications are possible within the scope of the claims. In the embodiment described above, it has been described that the thin film oscillator 31 is formed by a spin coat method. In the present invention, however, not limiting to this embodiment, a sheet-like thin film oscillator made up of a high-polymer material may be provided on a wafer.

EXAMPLES

Figure 8A:
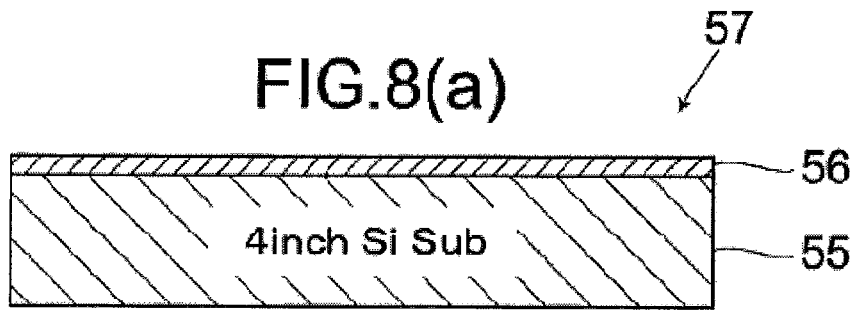
FIG. 8(a) is a cross-sectional view illustrating a substrate sample structure according to an embodiment in the present invention.
Figure 8B:
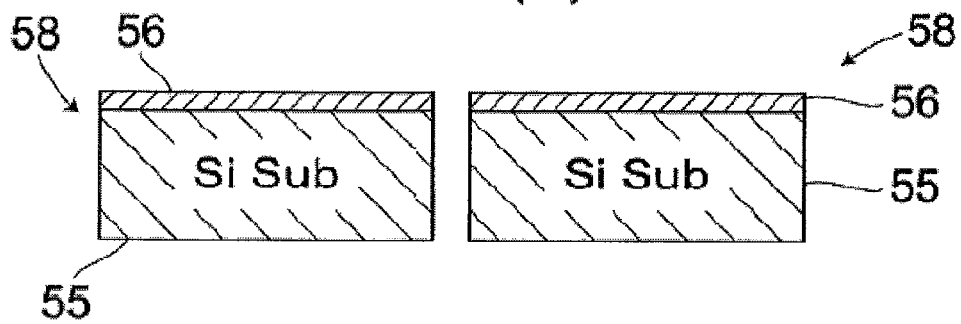
FIG. 8(b) is a cross-sectional view illustrating sample chip structures according to an embodiment in the present invention.

Next is a description of examples according to the present invention. First, as shown in FIG. 8(a), a substrate sample 57 was made by laminating a Ti thin film 56 into 200 mm in thickness on an Sb-doped N-type Si substrate 55 (its resistivity is 0.02 Ω·cm). Then, the substrate sample 57 was divided, as shown in FIG. 8(b) to obtain two or more 20 mm-square sample chips 58.

Figure 9:
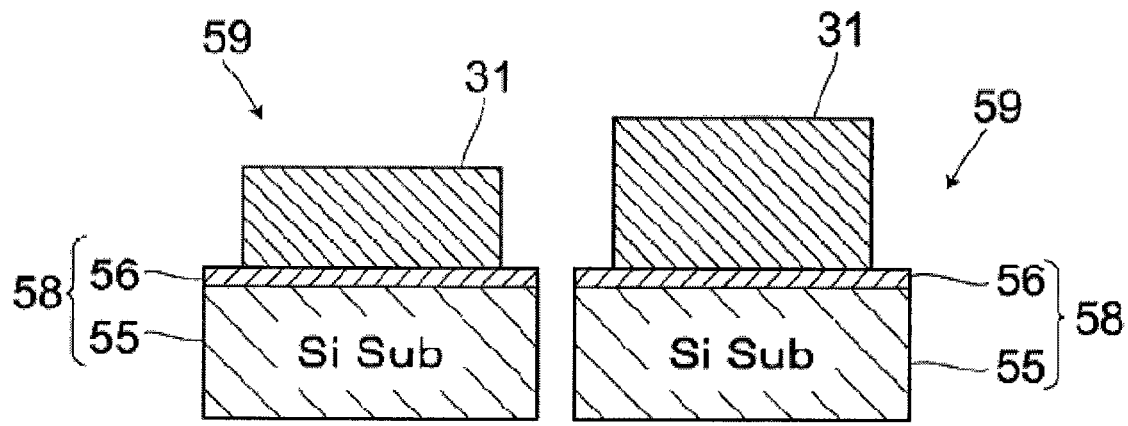
FIG. 9 is a cross-sectional view illustrating the sample structures according to an embodiment in the present invention.
Figure 10:
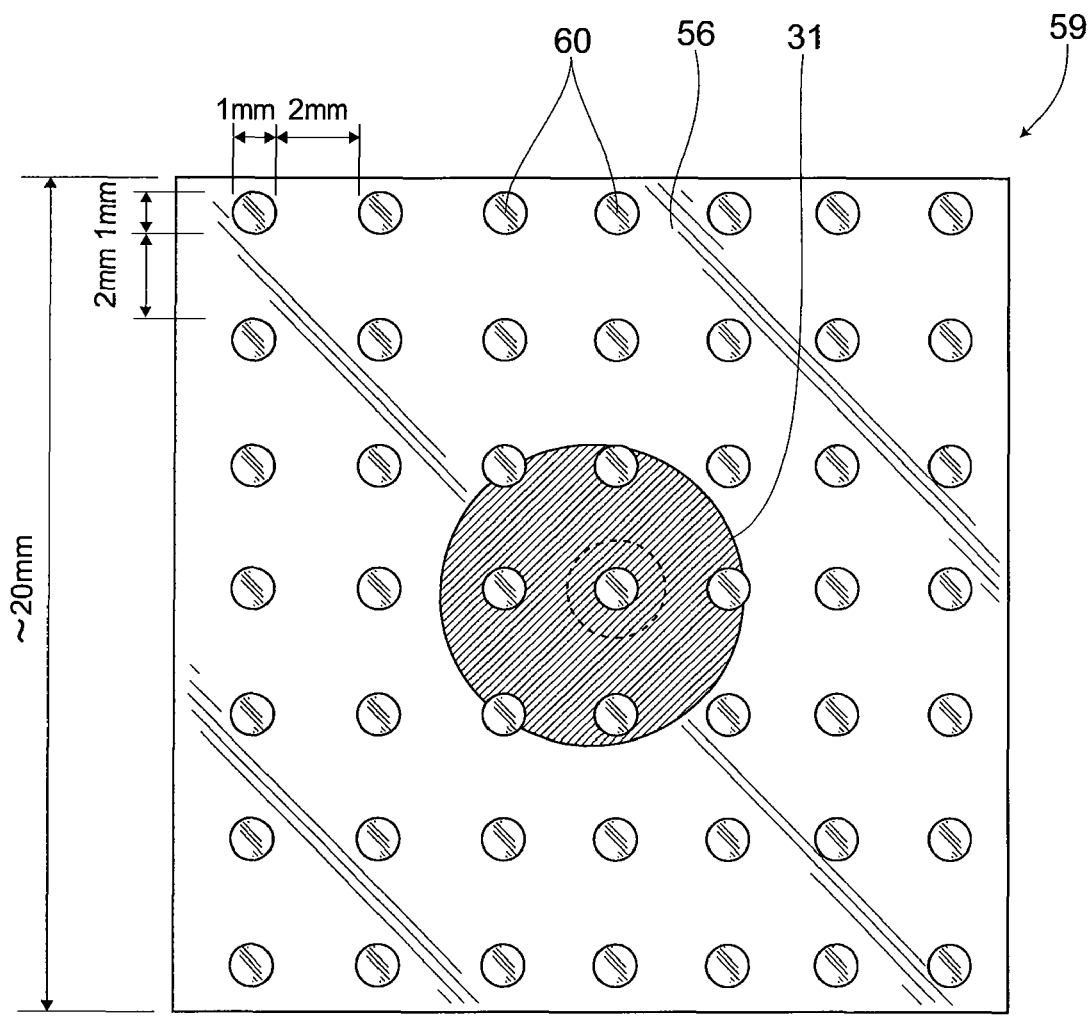
FIG. 10 is a plain view illustrating a sample structure according to an embodiment in the present invention.

A thin film oscillator 31 formed on each of sample chips 58 from P (VDF/TrFE) by using an application method was laminated, as shown in FIG. 9. Then, six samples 59 of the thin film oscillator 31 were prepared by forming each of the film's thickness into 2, 4, 6, 8, 10 and 12 μm. In addition, by using a vapor-deposition method, each of the thus obtained samples 59 was formed with Al electrodes positioned at regular intervals as shown in FIG. 10.

Figure 11:
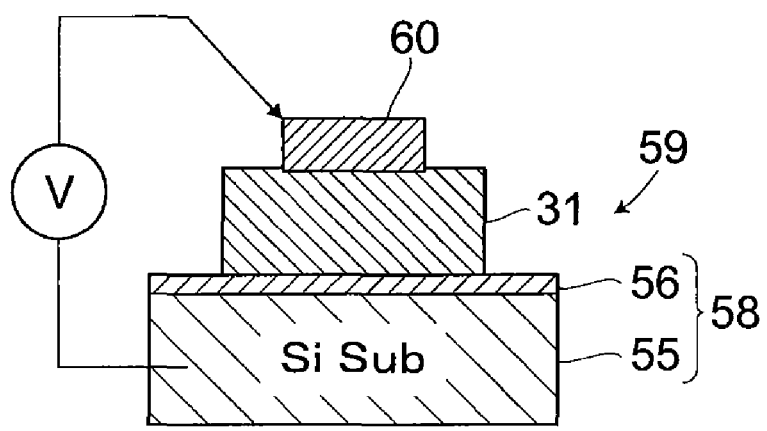
FIG. 11 is a cross-sectional view illustrating a structure in implementing an orientation treatment according to an embodiment in the present invention.

Then, as shown in FIG. 11, the Si substrate 55 and each of the Al electrodes 60 were electrically connected to apply an orientation treatment to the sample 59. As the orientation treatment, a voltage of 200V was applied for 30 minutes across the Si substrate 55 and each of the Al electrodes 60, with the sample 59 heated to a given temperature (180 degrees C. in the present embodiment) under the condition shown in the sequence in FIG. 12. Besides, in this case, in order to evaluate a withstand voltage of the thin film oscillator 31, a leak current was measured in conjunction with the applied voltage 200V. In addition, this orientation treatment condition was determined due to the fact that the Curie temperature, being the transition temperature where ferroelectrics changing into paraelectrics was 180 degrees C. for P(VDF/TrFE).

Figure 13:
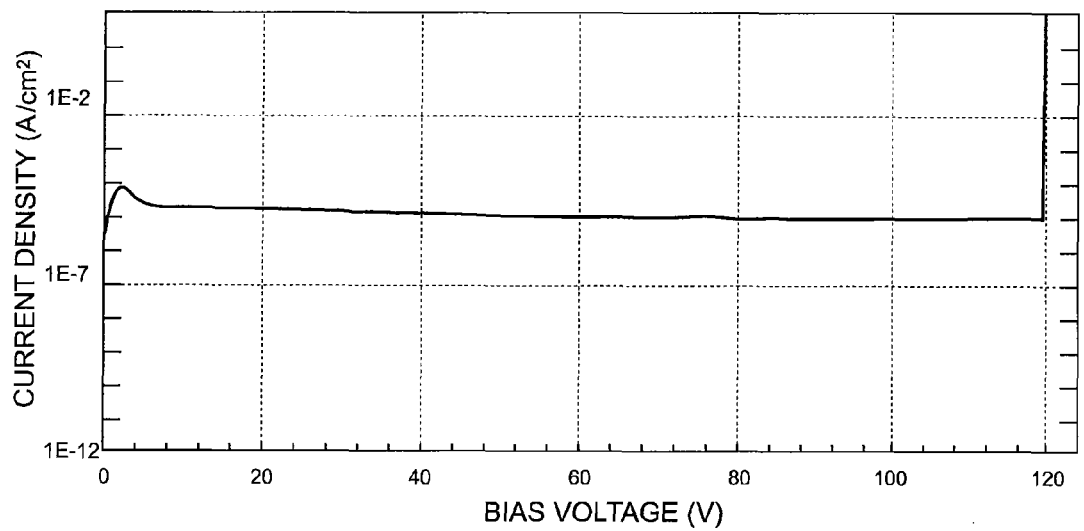
FIG. 13 is a diagrammatic view illustrating current density vs. voltage when the orientation treatment has been applied to a thin film oscillator with 10 μm in thickness, according to an embodiment in the present invention.
Figure 14:
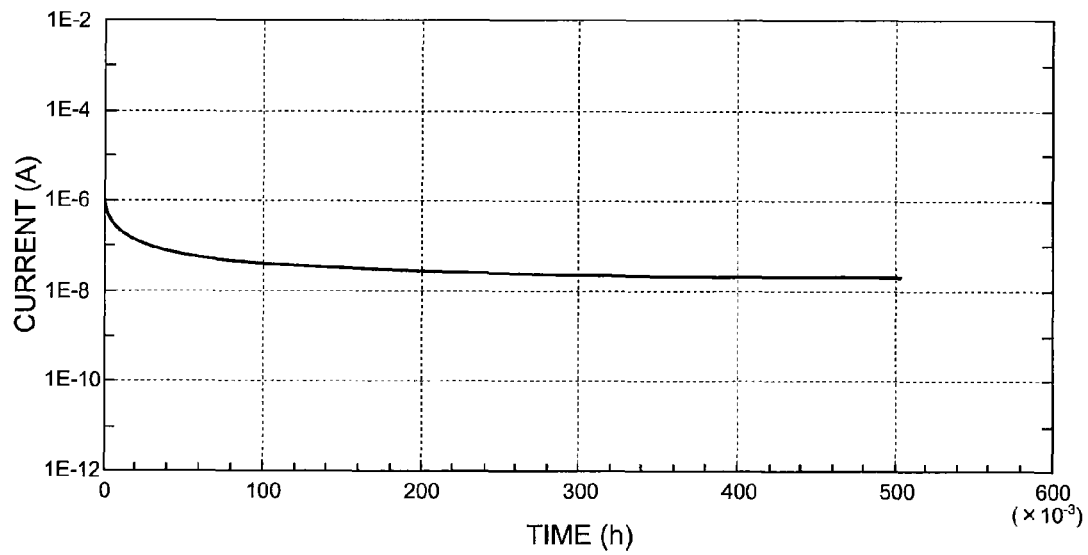
FIG. 14 is a diagrammatic view illustrating current vs. time when the orientation treatment has been applied to a thin film oscillator with 12 μm in thickness according to an embodiment in the present invention.

As a result, it has been verified (refer to FIG. 13) that in the sample of the thin film oscillator 31 with 10 μm in film thickness, at 119.5V before the voltage had reached 200V, the thin film oscillator 31 broke down to cause each of the Al electrodes 60 and the Si substrate 55 to be substantially short-circuited. Contrarily, it has been verified (refer to FIG. 14) that in the sample of the thin film oscillator 31 with 12 μm in film thickness, with 200V applied to the sample for 30 minutes, a leak current made by the transition with the small remaining leak current to permit the orientation treatment is to be normally practiced. Consequently, it has been ascertained that in the thin film oscillator 31 made up of P(VDF/TrFE), the orientation treatment could be certainly practiced. In addition, with respect to the film thickness of the thin film oscillator 31, by still examining a forming condition or the like, even if applying thinner film thickness, the orientation treatment described above can be estimated in realization.

Figure 15:
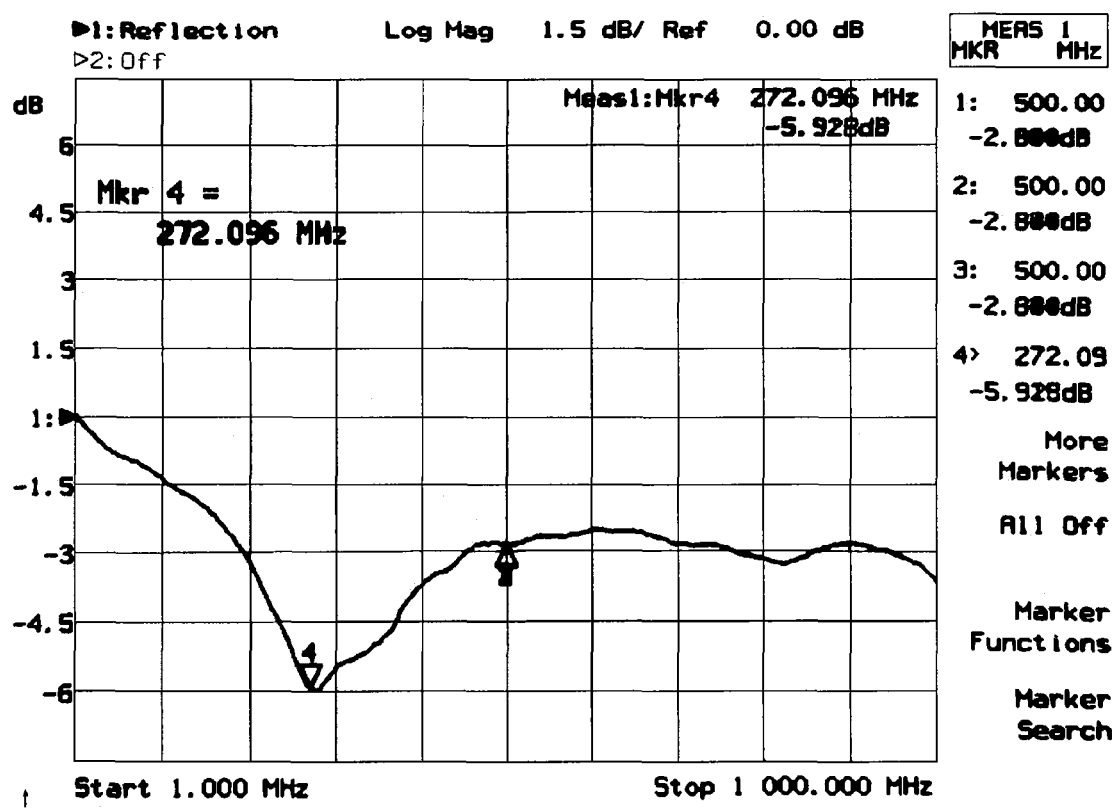
FIG. 15 is a diagram illustrating a characteristic frequency of insertion loss according to an embodiment in the present invention.

With regard to the samples thus obtained, a characteristic frequency of the insertion loss was measured (refer to FIG. 15). From the result, it has been checked that the resonant frequency sharply formed and thereby a sympathetic vibration was generated from the thin film oscillator 31.

Figure 16:
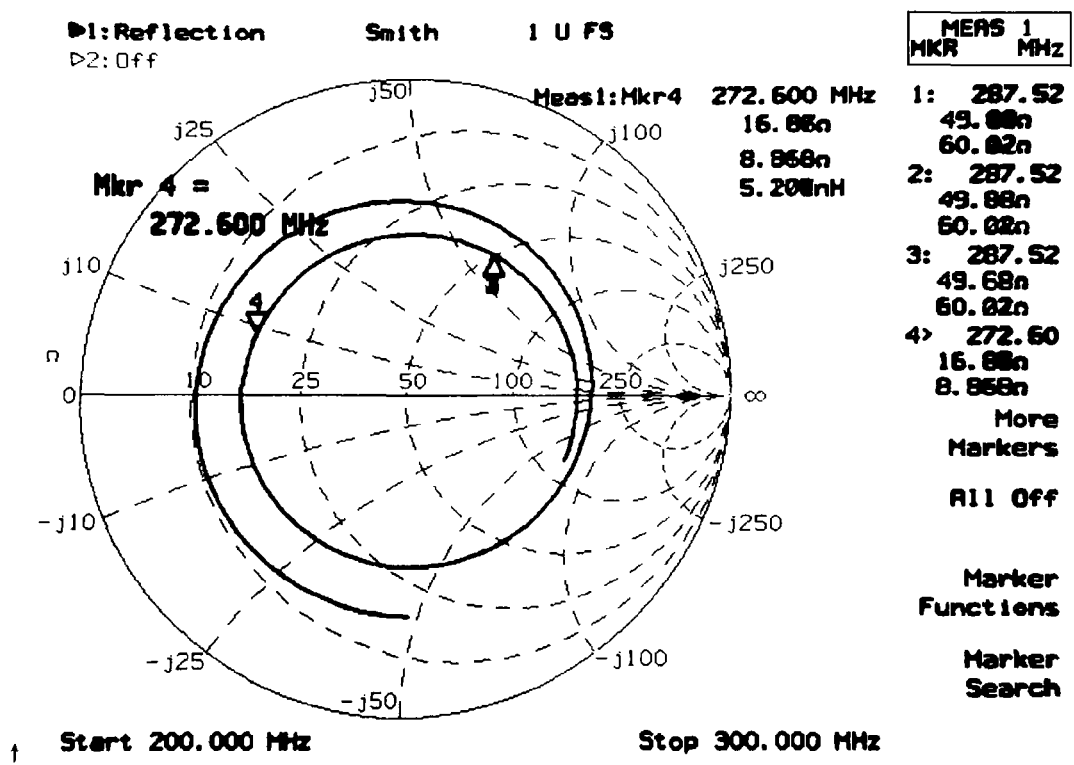
FIG. 16 is a smith chart according to an embodiment in the present invention.

Besides, in FIG. 16, a smith chart is shown which has been measured in the thus obtained samples. From the result, it has been checked that the resonance impedance of the thin film oscillator made up of P(VDF/TrFE) could be set as 50Ω.

Figure 12:
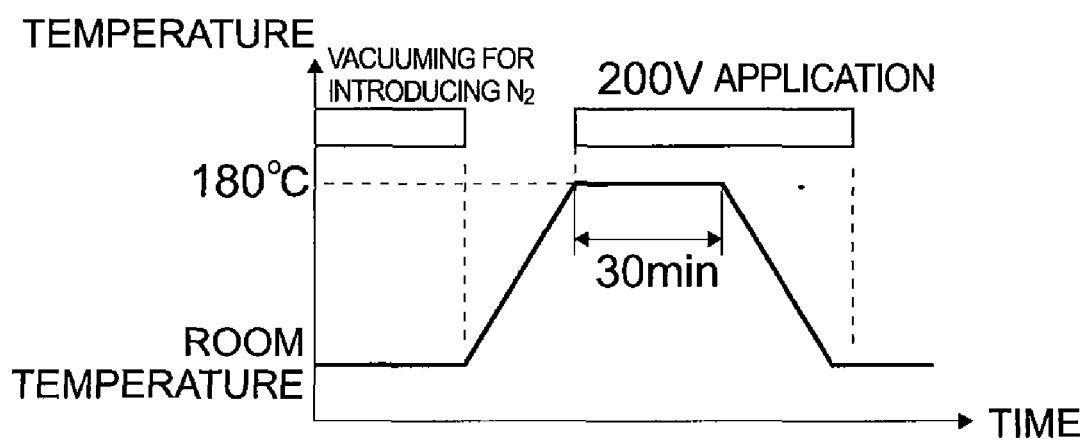
FIG. 12 is a diagram illustrating a sequence in implementing the orientation treatment according to an embodiment in the present invention.

Moreover, it has been checked that in the orientation sequence in FIG. 12, even when no voltage was applied across the Si substrate 55 and the Al electrode 60, the sympathetic vibration which is the same as that in FIG. 15 was checked although it was being weak compared to that in the above application of the voltage. Therefore, it has been verified that even by the orientation sequence without applying a voltage, an available thin film oscillator could be created which had an orientation performance nearly equal to that obtained by the orientation sequence (refer to FIG. 12) with an applied voltage.

The invention claimed is:

1. A quantitative evaluation device for an atomic vacancy existing in a silicon wafer, comprising:
   a silicon sample formed with an ultrasonic generator and an ultrasonic receiver on a silicon wafer,
   a magnetic force generator for applying an external magnetic field to the said silicon sample,
   a cooler capable of cooling the said silicon sample to a range of temperatures lower than or equal to 50 k,
   a detector for detecting a phase difference between an ultrasonic pulse generated from the said ultrasonic generator and a measured wave pulse created by allowing the said ultrasonic pulse to propagate within the said silicon wafer to be received in the said ultrasonic receiver,
   wherein the said ultrasonic generator and the said ultrasonic receiver are each equipped with a transducer including:
   a thin film oscillator with a physical property capable of following an expanding action of a silicon wafer in association with a temperature drop in the said range of temperatures and is made up of a high-polymer material having the nature of generating orientations of molecular axes in any one of cases where the said thin film oscillator is solidified, where after being solidified, the said thin film oscillator is heated, and where after being solidified, the said thin film oscillator is heated and then is cooled; and electrodes for applying an electric field to the said thin film oscillator.

2. A quantitative evaluation device according to claim 1, wherein the said thin film oscillator is made up of a high-polymer material having the solidifying nature with its molecular axes oriented in the direction of an external electric field applied to the said high-polymer material, said orientations of molecular axes being maintained even after removing the said external electric field.

3. A quantitative evaluation device according to claim 2, wherein in a highly-heated state at temperatures equal to or higher than 50 degrees C. and lower than or equal to 500 degrees C., an electric field is applied to the said thin film oscillator to orient molecular axes of the said thin film oscillator in the direction of the said electric field.

4. A quantitative evaluation device according to claim 1, wherein the said high-polymer material is PVDF or P(VDF/TrFE).

5. A quantitative evaluation device according to claim 1, wherein the said thin film oscillator is 0.1 to 30 μm in thickness.

6. A quantitative evaluation device according to claim 1, wherein the said ultrasonic pulse is allowed to propagate in the direction of a crystal orientation in which a ratio of an elastic constant $C_{44}$ is large, said measured wave pulse being received in the said ultrasonic receiver to detect a phase difference between the said ultrasonic pulse and the said measured wave pulse.

7. A quantitative evaluation device according to claim 1, wherein any one of a gold thin film, a titanium thin film, an aluminum thin film and a copper thin film is formed between surfaces of the said thin film oscillator and the said silicon sample.

8. A quantitative evaluation device according to claim 1, wherein the said ultrasonic generator and said ultrasonic receiver employ an ultrasonic pulse of 10 μs or less in width.

9. A quantitative evaluation method comprising:
   an orientation treatment step in which in a silicon sample formed with an ultrasonic generator and an ultrasonic receiver each of which includes a thin film oscillator made up of a high-polymer material having a physical property capable of following an expanding action of a silicon wafer in association with a temperature drop in a range of temperatures lower than or equal to 50K, orientations of molecular axes are generated in any one of cases where the said thin film oscillator is solidified onto the said silicon sample, where after being solidified onto the same, the said thin film oscillator is heated, and where after being solidified onto the same, the said thin film oscillator is heated and then is cooled, and
   a detection step in which in a range of temperatures lower than or equal to 50K, an external electric field is applied to the said ultrasonic generator to generate an ultrasonic pulse in the said ultrasonic generator and then this ultrasonic pulse is allowed to propagate within a silicon wafer to create a measured wave pulse, said measured wave pulse being received in the said ultrasonic receiver, thus detecting a phase difference between the said ultrasonic pulse and the said measured wave pulse.

10. A silicon wafer manufacturing method comprising: an evaluation step for quantitatively evaluating an atomic vacancy existing in the said silicon wafer by using the said quantitative evaluation method according to claim 9.

11. A thin film oscillator which has a physical property capable of following an expanding action of a silicon wafer in association with a temperature drop in a range of temperatures lower than or equal to 50 K, wherein the said thin film oscillator is used for a ultrasonic generator and a ultrasonic receiver which are utilized for a quantitative evaluation device for an atomic vacancy existing in a silicon wafer and are each equipped with
   a detector including an ultrasonic generator and an ultrasonic receiver,
   a silicon sample formed with the said ultrasonic generator and the said ultrasonic receiver on a silicon wafer,
   a magnetic force generator for applying an external magnetic field to the said silicon sample, and
   a cooler capable of cooling the said silicon sample to a range of temperatures lower than or equal to 50 K, wherein
   said thin film oscillator is made up of a high-polymer material having the nature of being solidified with its molecular axes oriented in the direction of an electric field applied to the said high-polymer material and then maintaining the orientations of molecular axes even after removing the said electric field.

* * * * *